(12) United States Patent
Davey

(10) Patent No.: US 7,500,383 B2
(45) Date of Patent: Mar. 10, 2009

(54) METHOD AND APPARATUS FOR MONITORING THE INTEGRITY OF COMPONENTS AND STRUCTURES

(75) Inventor: Kenneth John Davey, Osborne Park (AU)

(73) Assignee: Structural Monitoring Systems, Ltd., West Perth (AU)

( * ) Notice: Subject to any disclaimer, the term of this patent is extended or adjusted under 35 U.S.C. 154(b) by 0 days.

(21) Appl. No.: 11/260,882

(22) Filed: Oct. 27, 2005

(65) Prior Publication Data
US 2007/0107496 A1 May 17, 2007

Related U.S. Application Data
(63) Continuation-in-part of application No. 09/905,681, filed on Jul. 13, 2001, now abandoned.

(30) Foreign Application Priority Data
Sep. 8, 2001 (AU) .................... PR0018

(51) Int. Cl.
*G01M 3/26* (2006.01)
(52) U.S. Cl. .................... 73/49.2
(58) Field of Classification Search .......... 73/49.2, 73/38, 40.7, 49.8, 46
See application file for complete search history.

(56) References Cited

U.S. PATENT DOCUMENTS

| | | | |
|---|---|---|---|
| 2,430,122 A | 11/1947 | Grace | |
| 3,188,855 A | 6/1965 | Dega | |
| 3,918,291 A | 11/1975 | Pauly et al. | |
| 4,104,906 A | 8/1978 | Oertle | |
| 4,145,915 A | 3/1979 | Oertle | |
| 4,344,320 A | 8/1982 | Haupt et al. | |
| 4,350,038 A | 9/1982 | Soncrant | |
| 4,364,261 A | 12/1982 | Askwith et al. | |
| 4,532,795 A | 8/1985 | Brayman et al. | |
| 4,651,557 A | 3/1987 | Cholet | |
| 4,715,213 A | 12/1987 | McGreehan et al. | |
| 4,776,206 A | 10/1988 | Armstrong et al. | |
| 4,806,913 A | 2/1989 | Schmidt | |
| 4,862,731 A | 9/1989 | Gates | |
| 4,942,758 A | 7/1990 | Cofield | |
| 4,979,390 A | 12/1990 | Schupack et al. | |

(Continued)

FOREIGN PATENT DOCUMENTS
EP 0 177 433 8/1985

(Continued)

*Primary Examiner*—Michael Cygan
(74) *Attorney, Agent, or Firm*—Allen, Dyer, Doppelt, Milbrath & Gilchrist, P.A.

(57) ABSTRACT

A method for monitoring the integrity of a permeable structure that is disposed in an environment containing a fluid at ambient pressure is provided. At least one cavity is formed in or on the permeable structure. A source of first fluid is provided at a first pressure greater than the ambient pressure. The cavity is coupled to the source through a high-fluid-flow impedance to establish a flow of the first fluid through the permeable structure via the cavity. A rate of flow of the first fluid through the permeable structure is allowed to stabilize to a steady-state rate. A change in the steady-state flow rate of the first fluid through the permeable structure is monitored.

24 Claims, 8 Drawing Sheets

U.S. PATENT DOCUMENTS

| | | |
|---|---|---|
| 5,056,356 A | 10/1991 | Kuhns et al. |
| 5,078,005 A | 1/1992 | Krempel et al. |
| 5,205,173 A | 4/1993 | Allen |
| 5,295,391 A | 3/1994 | Mastandrea et al. |
| 5,390,533 A | 2/1995 | Schulte et al. |
| 5,398,541 A * | 3/1995 | Hijikata et al. .................. 73/38 |
| 5,404,747 A | 4/1995 | Johnston et al. |
| 5,412,978 A | 5/1995 | Boone et al. |
| 5,438,862 A | 8/1995 | Keating et al. |
| 5,544,520 A | 8/1996 | Graf et al. |
| 5,596,137 A | 1/1997 | Perry et al. |
| 5,770,794 A | 6/1998 | Davey |
| 6,223,587 B1 | 5/2001 | Chiocca |
| 2002/0029614 A1 * | 3/2002 | Davey ........................... 73/37 |

FOREIGN PATENT DOCUMENTS

| | | |
|---|---|---|
| SU | 1710929 A | 2/1992 |
| WO | 94/27130 | 11/1994 |

\* cited by examiner

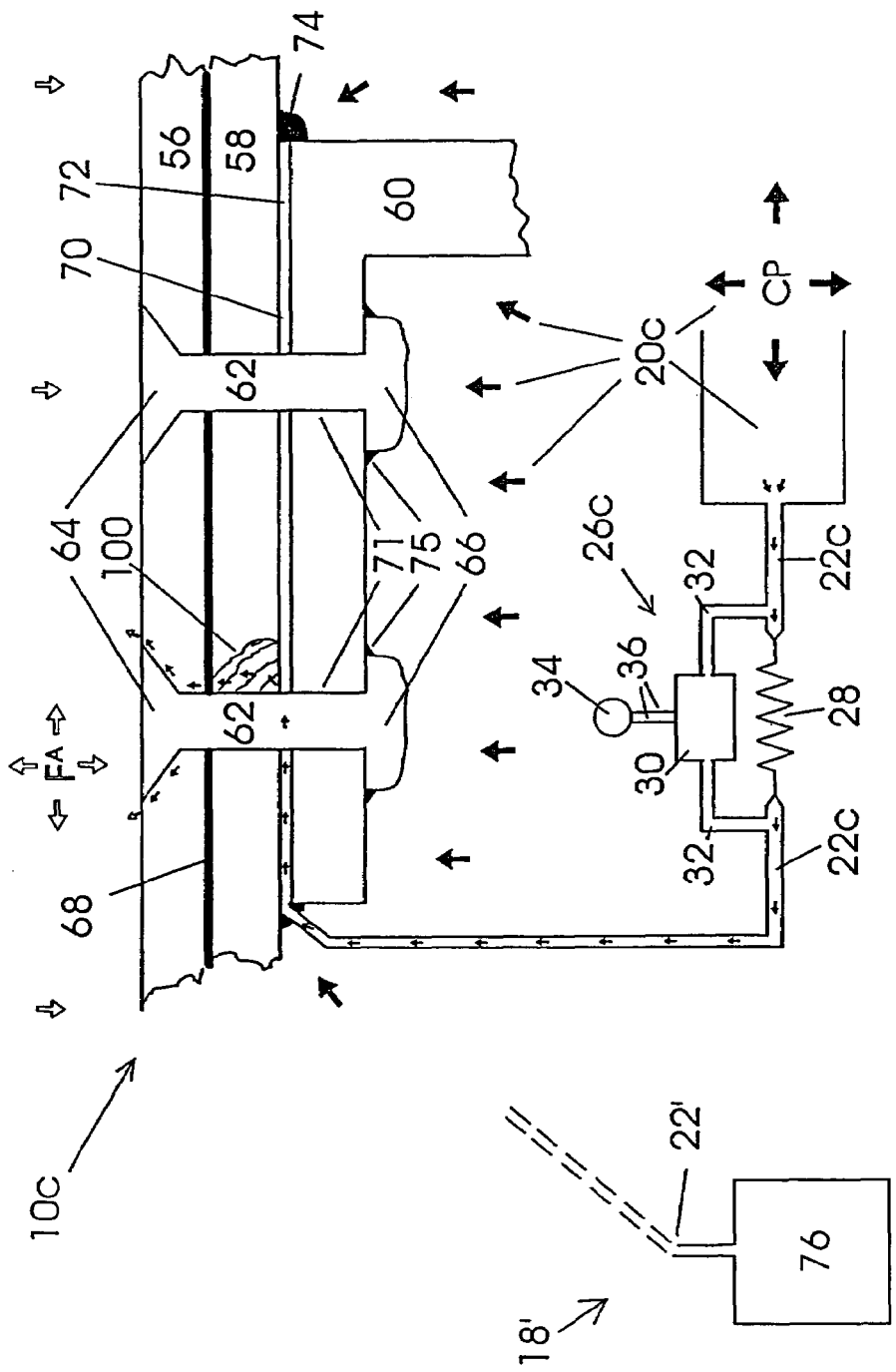

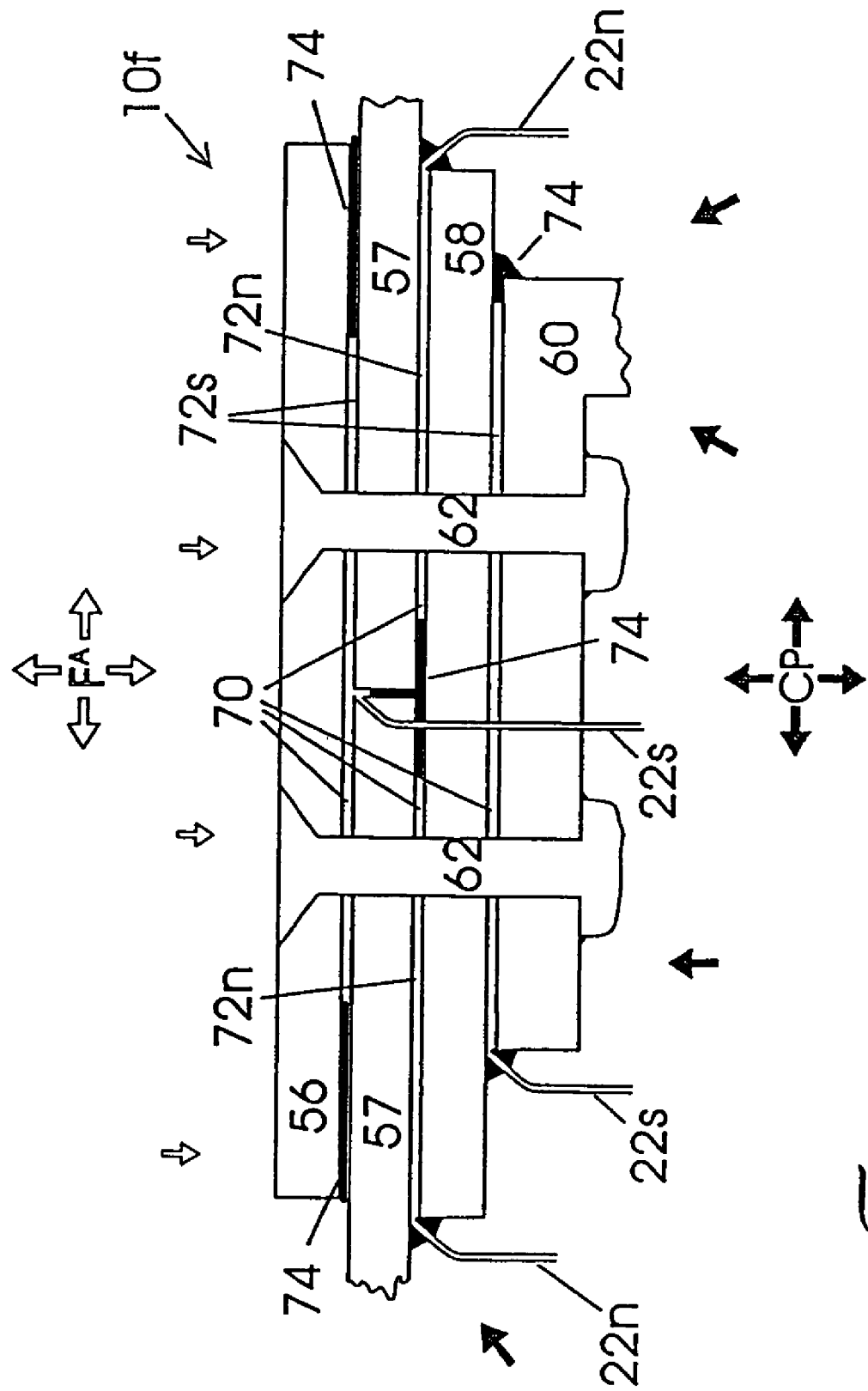

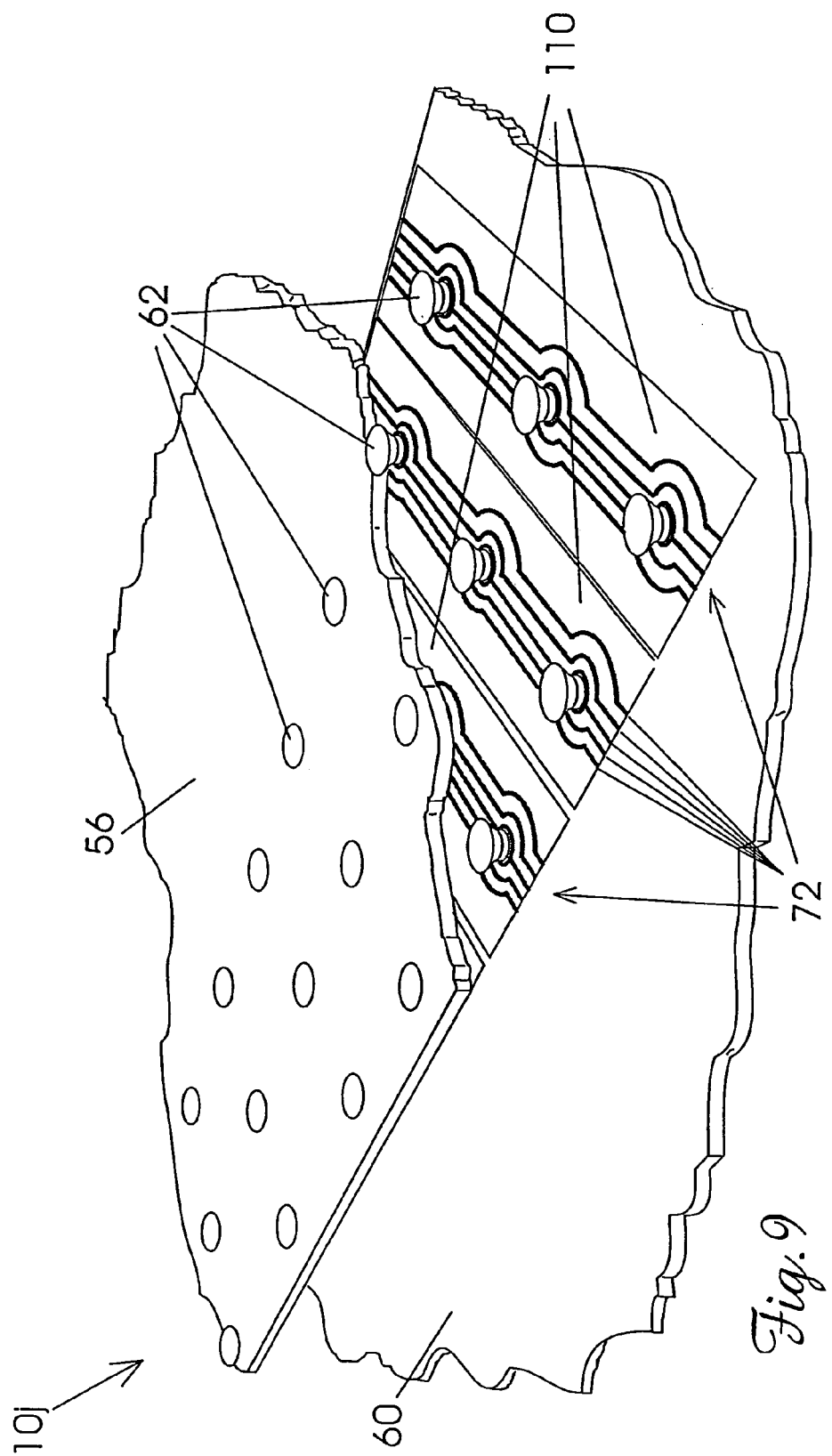

METHOD AND APPARATUS FOR MONITORING THE INTEGRITY OF COMPONENTS AND STRUCTURES

CROSS-REFERENCE TO RELATED APPLICATION

This application is a continuation-in-part of application Ser. No. 09/905,681, filed Jul. 13, 2001, which is now abandoned.

FIELD OF THE INVENTION

The present invention is for a method and apparatus for monitoring the integrity of a component or structure, in particular though not exclusively, by monitoring a pressure state that can be maintained within cavities either inherently provided or specifically formed in the component or structure.

BACKGROUND OF THE INVENTION

The present invention has its genesis from consideration of the problems faced by aircraft designers in monitoring the integrity of: sandwiched structures typically encountered around splices and cut-outs in fuselages; and, substantially hollow components as encountered in composite structures such as flaps, doors, panels and the like; and, attempting to prevent the ingress of moisture into such structures and components. These structures and components are difficult to examine for the detection of cracking, corrosion and disbonding. Further they are prone to the ingress of moisture arising for various reasons including: capillary action and the substantially hollow nature of the structures, particularly those made from composite materials; exposure to temperature extremes; exposure to large ambient pressure variations; exposure to environments of high humidity and precipitation.

Apart from corrosion in metallic structure, the ingress of moisture can lead to serious structural flaws such as disbanding due to progressive damage caused by the cyclic intrusion of the moisture followed by expansion as it freezes.

Of course the above problems are not the exclusive domain of aircraft designers. Structural integrity monitoring has very wide application and can be used, for example, to monitor the adhesive bonds such as between anechoic tiles on a submarine or heat resistant tiles on a spacecraft.

SUMMARY OF THE INVENTION

One embodiment of the invention provides a method of monitoring integrity of a permeable structure disposed in an environment containing a fluid at an ambient pressure at least one cavity being formed in or on the permeable structure, the method comprising:

providing a source of a first fluid at a first pressure greater than the ambient pressure;

coupling the at least one cavity to the source through a high fluid flow impedance to establish a flow of the first fluid through the permeable structure via the cavity;

allowing a rate of flow of the first fluid through the permeable structure to stabilise to a steady state rate; and, monitoring for a change in the steady state rate of flow of the first fluid though the permeable structure.

Another embodiment of the invention provides a method of constructing, and monitoring the integrity of, a permeable structure disposed in an environment containing a fluid at an ambient pressure, said method comprising the steps of:

constructing the permeable structure of one or more elements and forming at least one cavity in or on the permeable structure, wherein a portion of a surface of at least one of the structural elements forms a part of an internal surface of the cavity;

providing a source of a first fluid at a first pressure greater than the ambient pressure;

placing the at least one cavity in fluid communication with the source;

coupling a high fluid flow impedance in series between the at least one cavity and the source, the impedance being sufficiently high to create a pressure differential between said at least one cavity and said source resulting from a breach in the portion of the surface; and, monitoring for a change in differential pressure.

A further embodiment of the invention provides a method of monitoring the integrity of a permeable structure having an outer skin and an inner core of a honeycomb or cellular configuration composed of a plurality of adjoining cells, a number of the cells defining respective cavities internal of the permeable structure, the permeable structure disposed in an environment containing a fluid at an ambient pressure:

providing a source of a first fluid at a first pressure greater than the ambient pressure;

coupling at least one of the cavities to the source through a high fluid flow impedance to establish a flow of the first fluid through the permeable structure via the cavities;

allowing a rate of flow of the first fluid through the permeable structure to stabilise to a steady state rate; and, monitoring for a change in the steady state rate of flow of the first fluid through the permeable structure.

The first fluid source pressure may be substantially constant with respect to said ambient pressure.

In one embodiment the step of providing the first fluid source at the first pressure comprises setting the first pressure at a level which is sufficiently greater than the ambient pressure to overcome hygroscopic force and capillary action, but not sufficient to be detrimental to the integrity of the structure.

The first fluid may be a gas. In this event an embodiment of the invention may also comprise providing a moisture trap between the source and the at least one cavity to dry the gas prior to flowing into the permeable structure.

BRIEF DESCRIPTION OF THE DRAWINGS

FIG. 4a is a schematic representation of a further embodiment of the present invention;

FIG. 4b is a schematic representation of a further embodiment of the present invention;

FIG. 5b is a variation of the configuration of the embodiment of FIG. 5a;

FIG. 7 is a schematic representation of a four-layer sandwich structure to which an embodiment of the invention is applied;

DETAILED DESCRIPTION OF THE PREFERRED EMBODIMENTS

Figure 1:
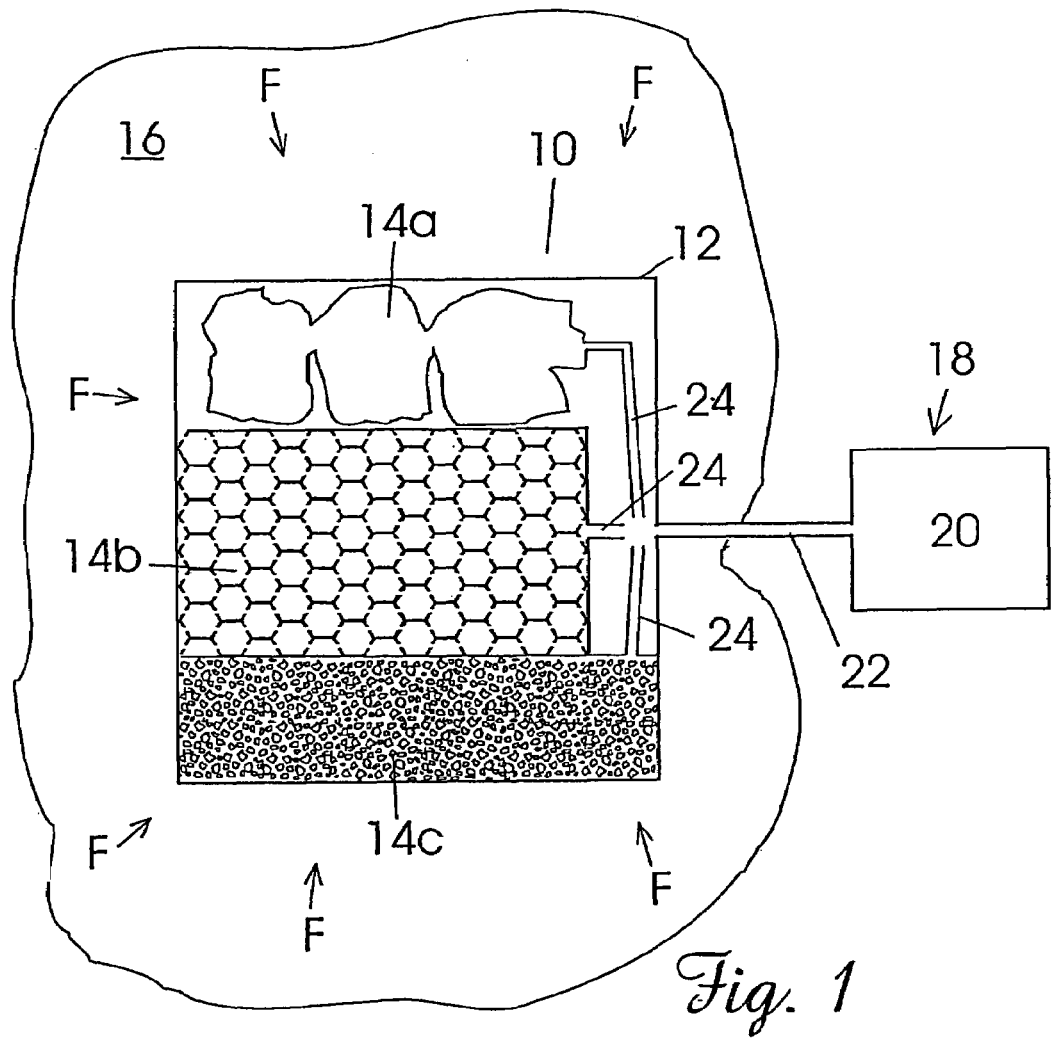
FIG. 1 is a schematic representation of a first embodiment of the present invention.

FIG. 1 illustrates schematically, one embodiment of a method and apparatus of the present invention for preventing the ingress of a fluid F into a structure 10. The structure 10 is a fictitious structure made up from three types of composite structure and is provided merely for the purpose of illustrating the principles of embodiments of the invention. The structure 10 has an outer skin 12 and a plurality of internal cavities 14a, 14b and 14c (hereinafter referred to in general as "cavities 14"). The actual geometry of the cavities 14 is a function of the type of structure 10. Cavities 14a are illustrative of a structure 10 having internal cavities of a random configuration; cavities 14b are illustrative of a structure 10 having a honeycomb or cellular-type core; and cavities 14c are illustrative of a structure 10 having a foam core.

The structure 10 is disposed in an environment 16 containing fluid F at an ambient pressure that acts on the structure 10. For example, the environment 16 may be the atmosphere at 4000 meters above sea level, where the fluid F is air; or the environment 16 may be the ocean at depth of 100 meters in which case the fluid F is sea water.

Apparatus 18 in accordance with an embodiment of the present invention acts to prevent or at least minimise the ingress of the fluid F into the structure 10. The apparatus 18 includes a pressure source 20 for providing a first fluid such as, air or an inert gas at a pressure higher than the pressure of the fluid F. A communication channel in the form of a conduit 22 provides fluid communication between the source 20 and one or more of the internal cavities 14 of the structure 10. If it is the case that the cavities 14 of structure 10 are all directly or indirectly in fluid communication with each other, then in order for the gas of source 20 to be in fluid communication with the cavities 14, the conduit 22 need only extend into the structure 10 to a point where it pierces the skin 12. Further, although not illustrated, a plurality of conduits 22 can be provided between the source 20 and the structure 10. However, if the cavities 14 are not in mutual fluid communication with each other or are arranged in sealed layers or groups, the communication path of apparatus 18 can include one or more galleries or conduits 24 contained within the skin 12 that communicate with the conduit 22 thereby providing fluid communication between the gas of the source 20 and the cavities 14. Alternately small perforations can be made between the internal cavities 14 to allow fluid communication there between. This may for example be achieved using a laser.

The pressure of source 20 is arranged to be greater than the pressure of fluid F (which may be either a static pressure or a dynamic pressure) so as to prevent the ingress of fluid F into the cavities 14. More particularly, the pressure of source 20 is arranged to be sufficient to overcome hygroscopic force and capillary action to prevent moisture ingress into the structure 10 but is not sufficient to be detrimental to the integrity of the structure 10.

It is to be recognised that if the skin 12 is absolutely impermeable to fluid F and such does not contain any faults or does not develop any faults throughout the life of the structure 10 then the fluid F of environment 16 cannot enter the structure 10. However, in practice, for a variety of reasons including the effects of material permeability, dynamic loading, localised impact damage, practical imperfections in the manufacture of structure 10, or the use of fasteners to fabricate the structure it is often the case that the skin 12 is, or in time becomes, permeable to the fluid F. Thus in practice the structure 10 has some degree of permeability. Hence fluid F communicated to the cavities permeates through the structure to the surrounding environment.

Figure 2:
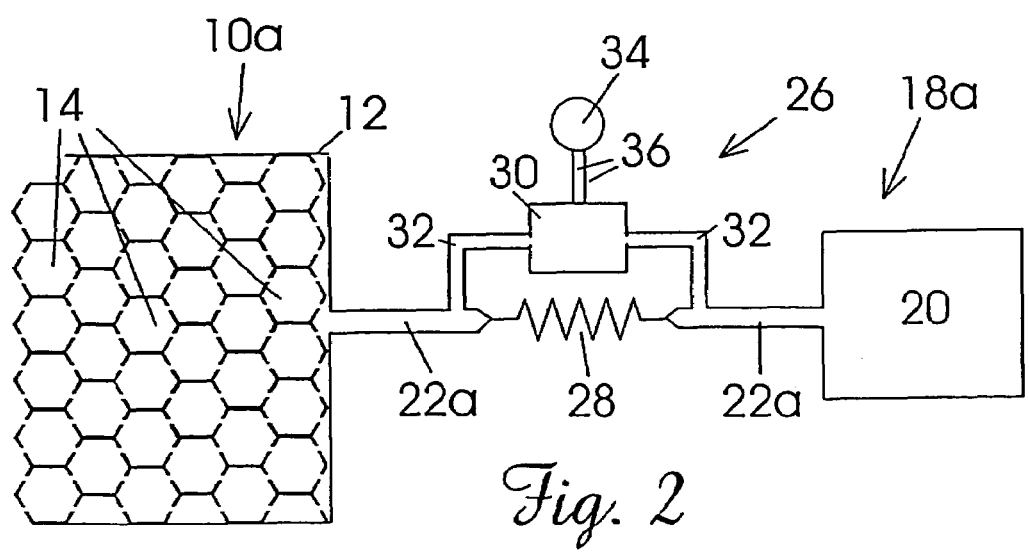
FIG. 2 is a schematic representation of an apparatus in accordance with a further embodiment of the present invention for monitoring the pressure state of cavities within a structure and hence the integrity of the structure.

FIG. 2 illustrates an apparatus 18a that allows for the monitoring of the pressure state of cavities 14 and hence the integrity of structure 10a. The apparatus 18a includes a fluid source 20 and a conduit 22a serving a similar function as conduit 22 in the embodiment depicted in FIG. 1 and interconnecting a monitoring device 26 for monitoring the inflow of fluid from the source 20 into the cavities 14. The monitoring device 26 is based on that disclosed in International Application No. PCT/AU94/00325 (WO 94/27130), the contents of which is incorporated herein by way of reference. The substantive difference being that a constant (positive) pressure source is employed in embodiments of the present invention, whereas in International Application No. PCT/AU94/00325 (WO 94/27130) a constant vacuum source is employed. The monitoring device 26 monitors for a change in the steady state rate of inflow of fluid from the source 20 into the cavities 14. In this embodiment the monitoring device 26 includes a high fluid flow impedance 28 disposed in series in the conduit 22a between the source 20 and the cavities 14. The high fluid flow impedance 28 preferably comprises a very long length of small bore duct which allows a minuscule flow of fluid. Alternatively, the high fluid flow impedance 28 could comprise a permeable material such as sintered glass. The impedance 28 is sufficiently high to create a minimum discernable pressure differential between the cavities and the source 20, as a result of permeability, and a measurable pressure differential between the cavities and source resulting from a breech (re crack or other failure) in the structure To gain an appreciation of the flow rates through the PCT/AU94/00325 (WO 94/27130) device, the maximum rate of flow is at the minimum that can be detected by current digital flow meters. As an example, a duct having a bore of less than 0.3 mm and a length in excess of 3 meters and experiencing an air pressure drop of 20 kPa across its length would have a flow of approximately 2-3 micro liters/minute. Bearing in mind that sensitivity of the device increases at an exponential rate as zero is approached and, if desired the magnitude of the high fluid flow impedance can be extended towards infinity, extremely small flow rates can be detected.

Generally, the magnitude of the high fluid flow impedance should be sufficiently high as to produce significant pressure drop across the high impedance in response to minuscule flow through the high impedance.

Measuring means in the form of a differential pressure transducer 30 is coupled across the impedance 28. The transducer 30 is coupled across the impedance 28 by fluid connecting ducts 32, and coupled to an amplifier and display 34 by electrical conductors 36. Alternatively, the differential pressure transducer 30 coupled across the impedance 28 may be in the form of a non-electrical indicator where electrical circuitry is not desirable.

Assuming that the skin 12 of the structure 10a has some degree of inherent permeability, after initial start up of the apparatus 18a, there will be a characteristic steady state rate of seepage of fluid through and from the structure 10a. If there is a change in the permeability of the skin 12/structure 10a, there will be a corresponding increase in the rate of inflow of the fluid from the source 20 into the structure 10a. This will be monitored and detected by the monitoring device 26. A typical application of this embodiment could be an aircraft door, flap, aileron, and the like supplied with nitrogen at a pressure above ambient.

Figure 3:
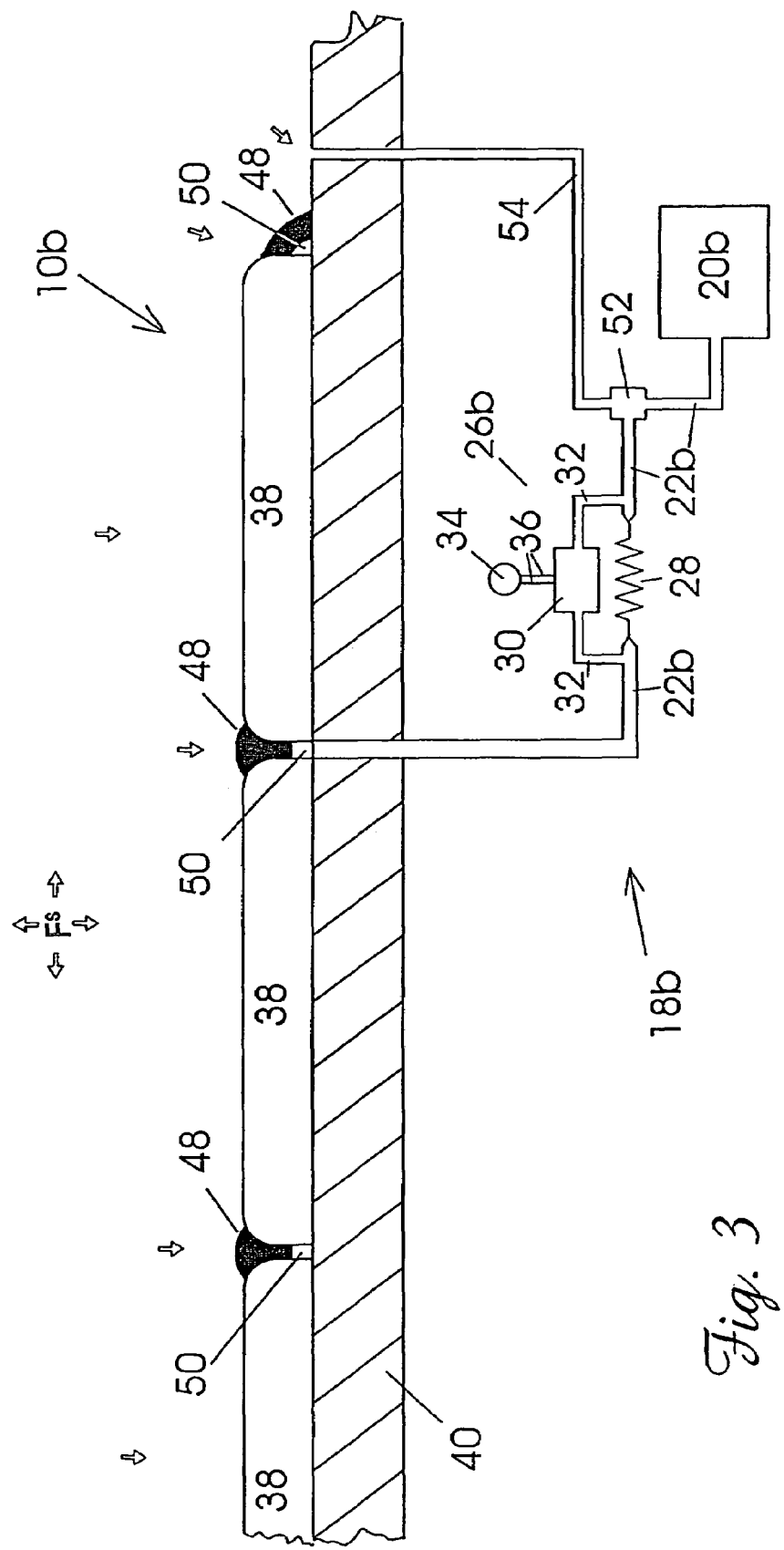
FIG. 3 is a schematic representation of a further embodiment of the present invention.

FIG. 3 depicts an embodiment of the present apparatus and method when applied to a structure 10b comprising anechoic tiles 38 adhered to the hull 40 of a submarine.

A fillet of elastomeric grout 48 is deposited about the periphery of each tile in a manner so that cavities 50 are created underneath the grout 48 between adjacent tiles 38 or, under grout 48 between the edge of a tile 38 and the adjacent surface of the hull 40. The cavities 50 are coupled to a monitoring apparatus 18b. The apparatus 18b is similar to the apparatus 18a depicted in FIG. 2 and encloses a monitoring device 26b which includes conduit 22b that provides a fluid communication path between the cavities 50 and a fluid source 20b (in this example a gas source) via a series connected high fluid flow impedance 28. Differential pressure transducer 30 is coupled across the impedance 28 via ducts 32. An amplifier and display 34 coupled to the transducer 30 via electrical conductors 36 provides a display of steady state pressure differential across the impedance 28. The fluid from supply 20 is metered through a pressure regulator 52 which is disposed in the conduit 22b between the impedance 28 and the source 20. The regulator 52 is also pressure referenced to the surrounding atmosphere, in this case sea water, herein shown with the notation F.sup.s and associated white pressure indicating arrow heads, via a duct 54. The regulator 52 maintains the pressure of the gas from source 20 at a substantially constant level above the water pressure. As ambient water pressure varies with depth the system 18b, and in particular the regulator 52, is able to dynamically vary the pressure of the gas from source 20 delivered to the cavities 50. In operation, the monitoring device 26b stabilizes with a relatively constant pressure differential across the high impedance irrespective of the ambient water pressure.

The integrity monitoring of the adhesive bonding of the tiles 38 is facilitated by monitoring the differential pressure across the high impedance 28 for any increase resulting from minuscule air seepage from any of the cavities 50 giving ample warning of any disbond of a tile 38 or damage to the grout 48. The imminence of disbanding and water ingress would be immediately obvious due to a rise in pressure differential across the impedance 28 and detected by the transducer 30. Loss of a tile 38 would result in a dramatic rise in differential pressure. The monitoring device 26b can also be provided with an adjustable bypass of the impedance 28 to allow high rates of flow of air from the source 20 to allow for some damage tolerance and maintain positive pressure protection for the cavities 50.

As ambient pressure of the sea water F.sup.s surrounding the hull 40 of the submarine would vary significantly from the top of the conning tower fin to the belly of the hull, it may be necessary to group the tiles 38 into several vertically tiered layers which are monitored separately to ensure that the pressure of the gas supplied to a particular group of tiles remains only slightly above the ambient pressure acting on those tiles thereby preventing excess positive pressure in upper groups of tiles. This can be achieved by providing a manifold in the portion of conduit 22b between the source 20 and regulator 52 and having a plurality of regulators 52 each feeding from the manifold and coupled to identical arrangements of high fluid flow impedance 28, transducer 30, and ambient pressure reference 54.

FIG. 4a illustrates a further embodiment of the present invention applied to a structure 10c comprising three components 56, 58 and 60 which are coupled in a sandwich construction. More particularly, the structure 10c is part of a pressurized fuselage of an aircraft. The components 56, 58 and 60 are fastened together by rivets 62 which pass through holes 71 formed in the components 56, 58 and 60. Each rivet 62 has a head 64 that sits flush with the component 56 and a flattened tail 66 at an opposite end that sits on the component 60. Flush head rivets are shown as an example but round head rivets and possibly bolt fasteners could be substituted.

Sandwich components generally have a layer of a sealant material between each fastened layer partly to prevent corrosion and fretting. To facilitate the provision of a cavity, this arrangement is modified in the present embodiment such that a sealant layer 68 is provided between components 56 and 58 only, with the sealant that would ordinarily exist between components 58 and 60 at least partially removed leaving a gas permeable gap 70 there between. In accordance with the present embodiment the gap 70 can be formed into a cavity 72 by providing a perimeter seal 74 about the perimeter of gap 70. Sealant 75 should also be employed sparingly around the flattened end 66 of rivets 62 and adjacent surface of component 60. Apparatus 18c, enclosing monitoring device 26c is connected to the cavity 72 for monitoring the integrity of the structure 10c. The monitoring device 26c includes a conduit 22c leading to a parallel connection of high fluid flow impedance 28 and pressure transducer 30. The transducer 30 is coupled to an amplifier and display 34 via electrical conductors 36. Alternatively, the differential pressure transducer 30 coupled across the impedance 28 may be in the form of a non-electrical indicator where electrical circuitry is not desirable.

The pressure source 20c of this embodiment is cabin pressure of the aircraft which feeds into both the impedance 28 and the transducer 30. The cabin pressure is marked as "CP" and has associated pressure indicating black arrow heads.

If a crack 100 was to form in the intermediate component 58 about the rivet 62, a fluid seepage flow path (indicated by small black flow indicating arrow heads) can be created around the rivet 62 and head 64 to the outside high altitude atmosphere F.sup.A, associated with white pressure indicating arrow heads, due to the crack 100 and subsequent loosening of the fastening. The resulting increase of the inflow of air into cavity 72 through the impedance 28 will be detected by the transducer 30 as a change in differential pressure thus providing an indication of the crack 100 in component 58.

In an alternate embodiment depicted in FIG. 4b, the apparatus 18' for monitoring the integrity of structure 10c comprises a compliant container 76 of a fluid marker such as a liquid or gaseous dye, or detectable gas, which is coupled by conduit 22' vice conduit 22c to the cavity 72. As with the previously described embodiment, if a crack 100 were to develop in the component 58 that extends to the rivet 62, there will be a flow of marker from the container 76 through conduit 22', cavity 72, the crack 100 and around rivet 62 to seep to the outside atmosphere. This arises because the compliant container 76 is also subject to cabin pressure CP. The detection of dye or gas about the rivet 62 provides an indication of the crack in the component 58.

When the fluid marker is a liquid, detection can be by means of visual inspection of the structure The appearance of the dye say around the head of a rivet 62 is potentially due to the existence of a crack. When a detectable gas is used as the marker, such as helium, gas monitoring and detecting equipment is required to detect the escape of the gas from the structure. In the case where the structure has some inherent permeability, there will be of course a steady state flow of the gas through the structure in which case one is required to monitor for a change in the steady state condition. On the other hand, if the structure is after initial manufacture absolutely impermeable, then one is required to detect for any presence of the gas marker. This of course is the same as monitoring for the appearance of a significant pressure differential across the monitoring apparatus 26c indicating a flow where previously no flow existed. However, because of the sensitivity of the fluid impedance device 26c, the fluid marker method is more likely to be useful in a secondary roll as an indicator of the location of a flaw.

Figure 5A:
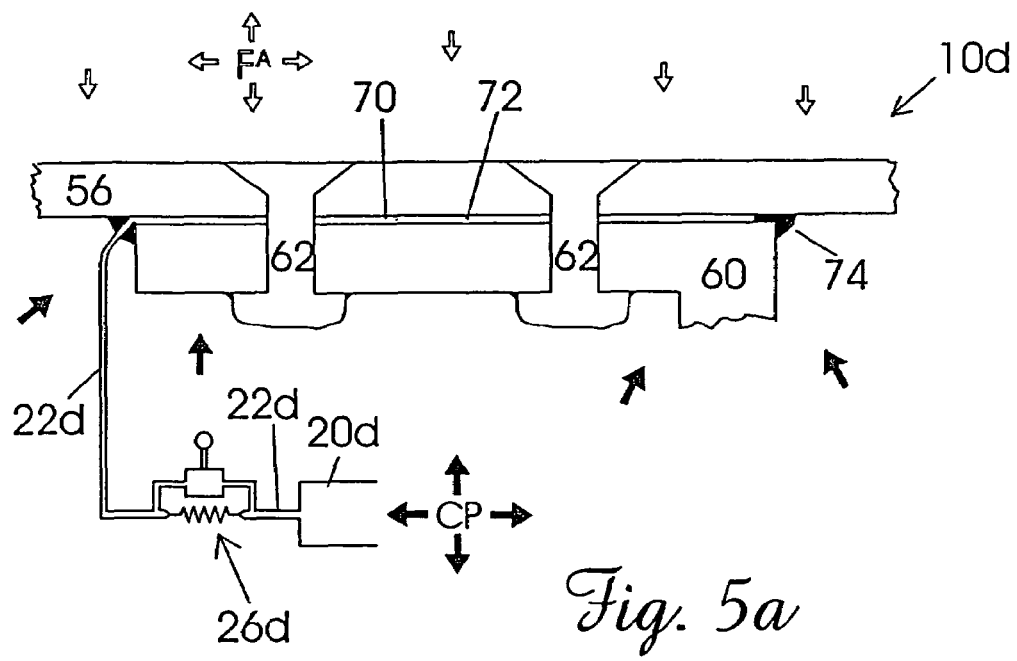
FIG. 5a is a schematic representation of a two-layer sandwich structure to which an embodiment of the present invention is applied.
Figure 5B:
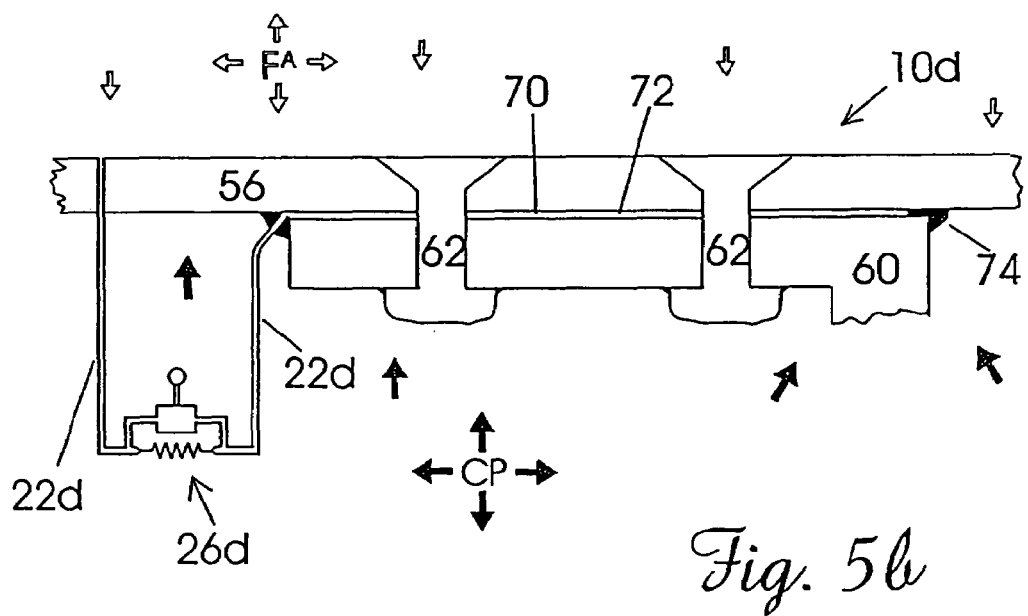
Figure 6:
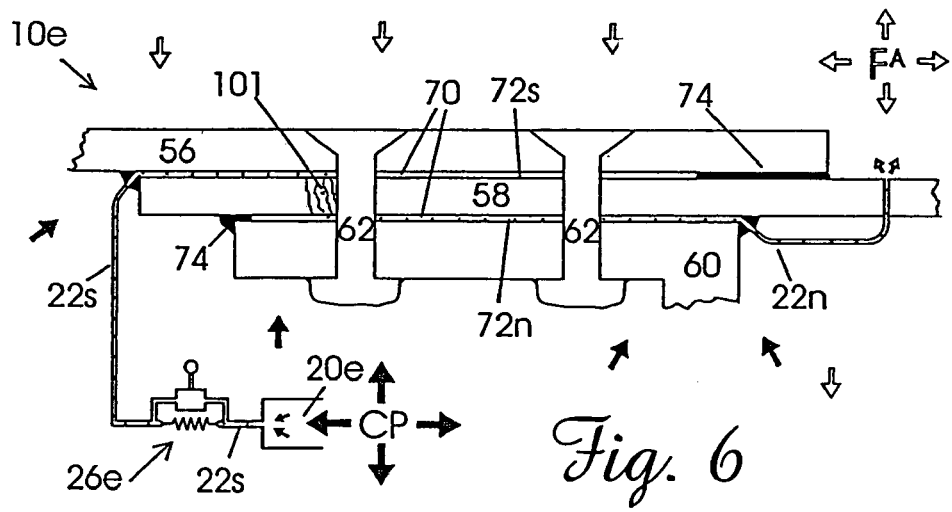
FIG. 6 is a schematic representation of a three-layer sandwich structure to which an embodiment of the present invention is applied.

FIGS. 5-7 depict variations of "sandwich" structures to which embodiments of the present invention can be applied.

In FIG. 5a, a portion of a structure 10d comprises two components 56 and 60 fastened together by rivets 62. A gas permeable gap 70 exists between mutually facing adjacent surfaces of components 56 and 60. A cavity 72 is formed by sealing the gap 70 with a perimeter seal 74. Similar to FIG. 4a, the structure 10d is a portion of an aircraft fuselage containing cabin pressure CP and is disposed in an environment of a fluid F.sup.A being ambient air pressure at high altitude. The integrity of the structure 10d can be monitored by connecting the cavity 72 via a conduit 22d to a monitoring apparatus 26d similar to 26c of FIG. 4a of the type described herein above.

As the cavity 72 in the structure 10d is completely enveloped by the fluid F, any seepage of gas from the cavity 72 through component 56 will be to the outside environment F.sup.A.

In a variation of the above arrangement of FIG. 5a, shown in FIG. 5b, the apparatus 26c could be connected between the cavity 72 and the outside atmospheric pressure F.sup.A. In this example, cavity 72 becomes a conduit for pressure source in form of cabin pressure (CP) in the event of a through flaw developing in component 60. This arrangement is further discussed in FIGS. 6a and 6b following.

In FIG. 6, the structure 10e is very similar to the structure 10c in FIG. 4a. However the structure 10e is now formed with two cavities, 72s and 72n. The cavity 72s is formed between mutually adjacent faces of components 56 and 58 of the structure 10e. The cavity 72s is in fluid communication via conduit 22s with the pressure source 20e (CP) via monitoring apparatus 26e of like structure and function as described above. The cavity 72n however which exists between components 58 and 60 is placed in fluid communication with fluid pressure referenced to the outside environment F.sup.A. This now allows for the detection of a crack 101 in the intermediate component 58 that extends between the cavities 72s and 72n other than directly to the outside environment F.sup.A through component 56. A dotted trail shows the flow path from pressure source 20e, through duct 22s and device 26e, cavity 72s, crack 101 cavity 72n, duct 22n and thence to the outside atmospheric "environmental" pressure F.sup.A.

Figure 6A:
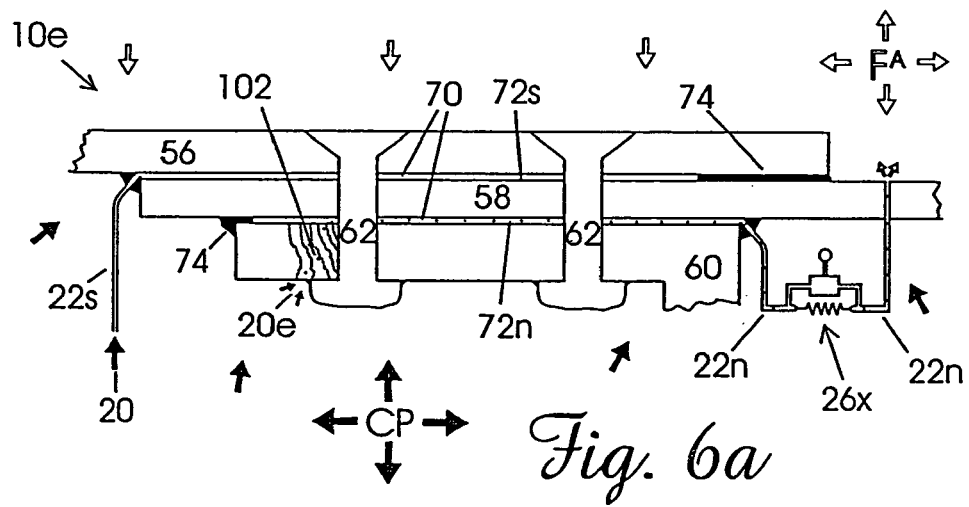
FIG. 6a is a variation of the configuration of the embodiment of FIG. 6.
Figure 6B:
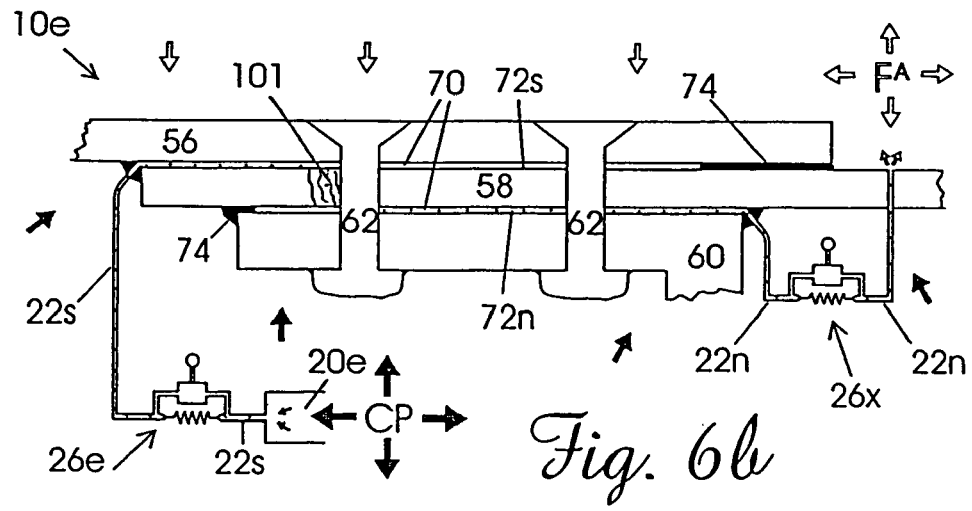
FIG. 6b is a further variation of the configuration of the embodiment of FIG. 6.

As a further measure, cavity 72n could be communicated via duct 22n to a similar apparatus to 26e (26x) and thence to an atmospheric pressure reference F.sup.A. This is shown in FIG. 6a and the employment of monitoring apparatus 26x is basically the same arrangement as shown in FIG. 5a. The purpose of this arrangement is to monitor the integrity of component 60. A crack or flaw 102 developing in component 60 communicating cabin pressure CP (source 20e) with cavity 72n would produce a pressure drop, due to seepage flow (small arrow heads and dots), across the fluid impedance of the apparatus 18x to the outside environmental F.sup.A. If this feature was desired, the connection of apparatus 26x could be normally bypassed or carried out at intervals to prevent a continuous series connection of two monitoring devices 26e and 26x (as shown in FIG. 6b) which would halve the sensitivity of both apparatus 26e and 26x in response to a flaw 101 occurring in component 58. Seepage flow from cavity 72s through a crack (101) in component 58, into cavity 72n, would have to pass through the two high fluid impedances in series of monitor 26e and 26x and the two associated differential pressure sensors would share the pressure drop resulting in halved sensitivity. The series flow problem is shown by small arrowheads and dots. Of course, if a crack developed in component 56 direct to the outside environmental F.sup.A, no such problem would arise.

FIG. 7 depicts a further sandwich structure 10f having four layers or sheets 56, 57, 58 and 60 connected together by rivets 62. Layer 57 comprises two abutted sheets. Structure 10f is once again a portion of an aircraft fuselage containing cabin pressure CP and is disposed in an environment of a fluid being ambient air pressure at high altitude. The method of monitoring the integrity of structure 10f includes forming cavities 72s that are in fluid communication, via conduits 22s, with the pressure source CP of a monitoring apparatus of the type described herein above typically 26c to 26x and forming cavities 72n that are in fluid communication via conduits 22n with the environmental ambient pressure F.sup.A, with cavities 72n interspersed between cavities 72s. The arrangement for monitoring the integrity of component 60 of FIGS. 5a and 6a could similarly be applied to FIG. 7.

Figure 8A:
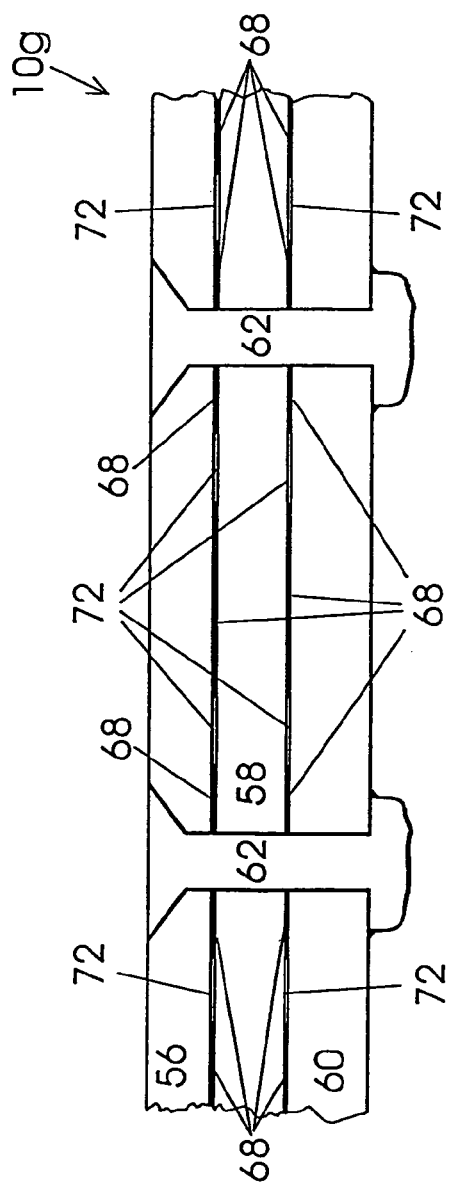
FIG. 8a is a schematic representation of a three-layer sandwich structure to which an embodiment of the present invention is applied.

FIG. 8a depicts a further embodiment of the invention. This embodiment is applied to a structure 10g comprised of three sheets 56, 58 and 60 formed as a sandwich construction coupled together by rivets 62. As explained in relation to the embodiment depicted in FIG. 4a, it is common for such structures to incorporate a layer of sealant material 68 between adjacent sheets. The layer 68 is typically provided to prevent corrosion and fretting of the sheets 56, 58, 60 about the rivets 62. In the present embodiment, the step of providing cavities 72 within the structure 10g involves removing sections of the sealant 68 between adjacent pairs of sheets. However areas of sealant 68 are maintained about the rivets 62 to maintain the function of minimizing fretting of the sheets 56, 58, and 60, and also to form boundary seals for the cavities 72. The removed sealant 68 produces the sealed cavities 72 which can be placed in fluid communication with a pressure source. Indeed alternate cavities 72 can be placed in fluid communication with the atmosphere and with the source as described above in relation to the embodiments depicted in FIGS. 6 and 7. The removal of the sealant 68 to produce the cavities 72 is ideally achieved during the construction of the structure 10g by placing masks on the sheets 56, 58 and 60 to prevent the depositing of sealant 68 in selected regions. After the sealant layer 68 has been applied and the masks removed, the structure 10g is pulled together by fastening with rivets 62.

Figure 8B:
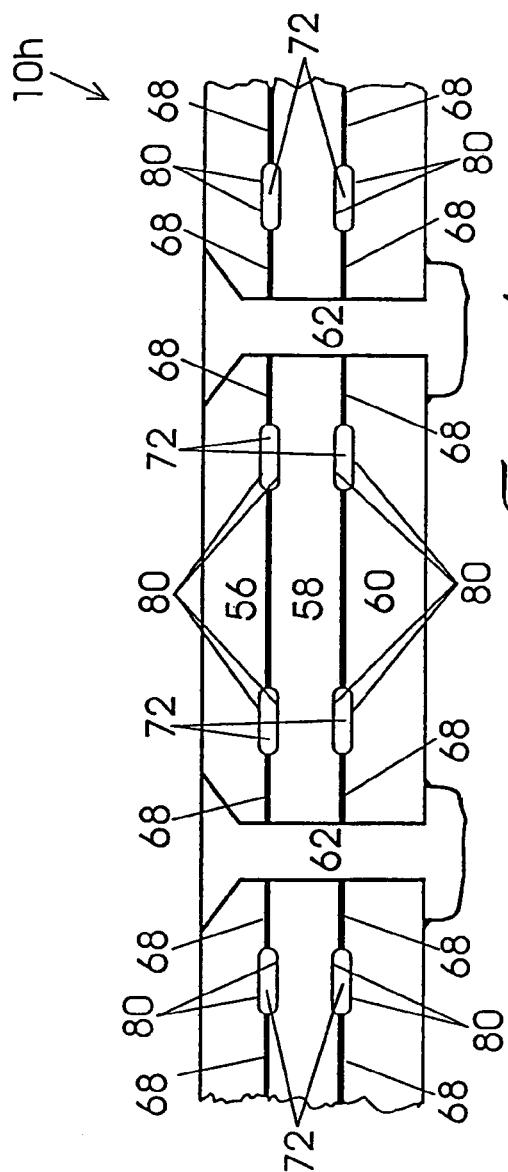
FIG. 8b is a schematic representation of a three-layer sandwich structure to which a further embodiment of the present invention is applied; and, FIG. 9 shows a partly sectioned oblique view of a further cavity arrangement.

FIG. 8b depicts a structure 10h which differs from that depicted in FIG. 8a by the inclusion of recesses or depressions 80 deliberately formed in the surface of the sheets 56, 58 and 60 in the regions where the sealant 68 is removed. This provides larger, more definite cavities 72. The recesses or depressions 80 can be formed by any known means including but not limited to, chemical milling. The cavities 72 can be placed in fluid communication with a constant pressure source by conduits typical of 22c to 22x in the manner described herein above in relation to FIGS. 4a-7. Of course in a further variation alternate cavities 72 can be placed in communication with the source 20 (CP) and the ambient pressure F.sup.A.

FIG. 9 shows a partly sectioned oblique view of a further structure in the form of lap splice 10*j* in which preformed elastomeric, self adhesive, film pads 110 are sandwiched between sheets 56 and 60 which are fastened together by rivets 62. The pads 110 comprise shapes cut and assembled so as to define multiple cavities 72 when sandwiched between the plates 56 and 60. For drawing convenience, the cavities 72 as shown as thick lines. By interspersing the connections of the cavities 72 with both atmospheric pressure reference and with cabin pressure interconnected to the monitoring apparatus typical of 26*c* to 26*e* of previous examples, cracks that may transit a sheet surface 56 or 60, before breaking through the either sheet, may be detected early. This is important because of the zipper effect of rapid failure in aircraft fuselages that have occurred in the past as cracks were not readily visible. By reversing the cabin pressure/ambient pressure relationship sequentially, to the three cavities shown either side of each rivet 62, confirmation of the growth of a crack, by recording a second interception can be achieved to aid the elimination of false positives. For additional reference, the examiner is directed to the specification International Application No PCT/AU94/00325 (WO 94/27130) which shows disclosure of crack detection.

Now that the embodiments of the present invention have been described in detail it will be apparent to those skilled in the relevant arts that numerous modifications and variations may be made without departing from the broad inventive concepts. For example, a moisture trap can be provided between the source 20 and impedance 28, when the source 20 is a gas source to dry the gas prior to flowing into the structure 10. Additionally, the source 20 can be a source of an inert gas. Further, anti corrosion agents can be induced into the defined cavities. When the structure 10 is a composite material having a plurality of internal cavities that are sealed from each other, embodiments of the invention include forming communication paths in the composite material between the internal cavities. All such modifications and variations are deemed to be within the scope of the present invention the nature of which is to be determined from the above description and the appended claims.

The invention claimed is:

1. A method of constructing, and monitoring the integrity of, a permeable structure disposed in an environment containing a fluid at an ambient pressure, said method comprising the steps of:
   constructing the permeable structure of one or more elements and forming at least one cavity in or on the permeable structure, wherein a portion of a surface of at least one of the structure elements forms a part of an internal surface of the cavity;
   providing a sealant or bonding material capable of maintaining a seal under a source of a first fluid at a first pressure greater than the ambient pressure;
   placing the at least one cavity in fluid communication with the source;
   coupling a high fluid flow impedance in series between the at least one cavity and the source, the impedance being sufficiently high to create a pressure differential between said at least one cavity and said source resulting from a breach in the portion of the surface; and
   monitoring for a change in differential pressure.

2. The method according to claim 1 wherein, a difference in pressure between the first pressure and the ambient pressure is held substantially constant.

3. The method according to claim 2 wherein, the step of providing the source comprises setting the first pressure at a level which is sufficiently greater than the ambient pressure to overcome hygroscopic force and capillary action, but not sufficient to be detrimental to the integrity of the permeable structure.

4. The method according to claim 3 wherein, said step of providing the source of first fluid comprises providing a source of a first gas.

5. The method according to claim 1 wherein when the permeable structure includes two or more internal cavities, the placing step comprises one or both of (a) placing the internal cavities in fluid communication with each other; and, (b) placing the internal cavities in fluid communication with the source.

6. A method according to claim 1 wherein forming the at least one cavity comprises laying a sealant material across the portion of the surface of each of the at least two structural elements.

7. The method according to claim 1 wherein, the constructing of the permeable structure comprises: joining together of two or more structural elements with at least one mechanical joiner.

8. The method according to claim 7 wherein, a portion of a surface of at least one of the or each joiner form a part of the internal surface of the cavity.

9. The method according to claim 1 wherein, the constructing step comprises constructing the permeable structure as a composite comprising an inner core of a honeycomb or cellular configuration composed of a plurality of adjoining cells and an outer skin surrounding the inner core wherein, one or more of the cells form respective cavities.

10. A method of constructing, and monitoring the integrity of, a permeable structure disposed in an environment containing a fluid at an ambient pressure, said method comprising the steps of:
   constructing the permeable structure of one or more elements and forming at least one cavity in or on the permeable structure, wherein a portion of a surface of at least one of the structure elements forms a part of an internal surface of the cavity;
   providing a sealant or bonding material capable of maintaining a seal under a source of a first fluid at a first pressure sufficiently greater than the ambient pressure to overcome hygroscopic force and capillary action;
   placing the at least one cavity in fluid communication with the source;
   coupling a high fluid flow impedance in series between the at least one cavity and the source, the impedance being sufficiently high to create a pressure differential between said at least one cavity and said source resulting from a breach in the portion of the surface; and
   monitoring for a change in differential pressure.

11. The method according to claim 10 wherein, a difference in pressure between the first pressure and the ambient pressure is held substantially constant.

12. The method according to claim 10 wherein, said step of providing the source of first fluid comprises providing a source of a first gas.

13. The method according to claim 10 wherein when the permeable structure includes two or more internal cavities, the placing step comprises one or both of (a) placing the internal cavities in fluid communication with each other; and, (b) placing the internal cavities in fluid communication with the source.

14. A method according to claim 10 wherein forming the at least one cavity comprises laying a sealant material across the portion of the surface of each of the at least two structural elements.

15. The method according to claim 10 wherein, the constructing of the permeable structure comprises: joining together of two or more structural elements with at least one mechanical joiner.

16. The method according to claim 15 wherein, a portion of a surface of at least one of the or each joiner form a part of the internal surface of the cavity.

17. The method according to claim 10 wherein, the constructing step comprises constructing the permeable structure as a composite comprising an inner core of a honeycomb or cellular configuration composed of a plurality of adjoining cells and an outer skin surrounding the inner core wherein, one or more of the cells form respective cavities.

18. The method according to claim 12 wherein, a difference in pressure between the first pressure and the ambient pressure is held substantially constant.

19. The method according to claim 18 wherein, the step of providing the source comprises setting the first pressure at a level which is sufficiently greater than the ambient pressure to overcome hygroscopic force and capillary action, but not sufficient to be detrimental to the integrity of the permeable structure.

20. The method according to claim 19 wherein, said step of providing the source of first fluid comprises providing a source of a first gas.

21. A method of constructing, and monitoring the integrity of, a permeable structure disposed in an environment containing a fluid at an ambient pressure, said method comprising the steps of:

constructing the permeable structure of two or more structural elements and forming at least one cavity in or on the permeable structure by laying a sealing or bonding material across a portion of a surface of each of the at least two structural elements to form at least two internal cavities, wherein the surface portion forms a part of an internal surface of the cavity;

wherein the sealing or bonding material is capable of maintaining a seal under a source of a first fluid at a first pressure greater than the ambient pressure;

placing the at least two cavities in fluid communication with each other and with the source;

coupling a high fluid flow impedance in series between the at least one cavity and the source, the impedance being sufficiently high to create a pressure differential between said at least one cavity and said source resulting from a breach in the portion of the surface; and monitoring for a change in differential pressure.

22. The method according to claim 21 wherein, the constructing of the permeable structure comprises: joining together of two or more structural elements with at least one mechanical joiner.

23. The method according to claim 22 wherein, a portion of a surface of at least one of the or each joiner form a part of the internal surface of the cavity.

24. The method according to claim 21 wherein, the constructing step comprises constructing the permeable structure as a composite comprising an inner core of a honeycomb or cellular configuration composed of a plurality of adjoining cells and an outer skin surrounding the inner core wherein, one or more of the cells form respective cavities.

* * * * *